United States Patent [19]
Bernhard et al.

[11] 3,951,679
[45] Apr. 20, 1976

[54] COLORED PIGMENTS

[75] Inventors: Horst Bernhard; Alfred Stein; Reiner Esselborn; Reiner Hesse; Horst Russmann, all of Darmstadt, Germany

[73] Assignee: Merck Patent Gesellschaft mit beschrankter Haftung, Darmstadt, Germany

[22] Filed: Mar. 15, 1974

[21] Appl. No.: 451,388

[30] Foreign Application Priority Data
Mar. 17, 1973  Germany............................ 2313332

[52] U.S. Cl.................................. 106/291; 106/304; 106/300; 106/308 B; 106/299; 424/63
[51] Int. Cl.².......................................... C09C 1/00
[58] Field of Search................ 106/291, 308 B, 304

[56] References Cited
UNITED STATES PATENTS

| | | | |
|---|---|---|---|
| 3,711,308 | 1/1973 | Brand et al. | 106/291 |
| 3,874,890 | 4/1975 | Bernhard | 106/291 |

*Primary Examiner*—Winston A. Douglas
*Assistant Examiner*—J. V. Howard
*Attorney, Agent, or Firm*—Millen, Raptes & White

[57] ABSTRACT

Blue colored mica flake pigments are provided by coating mica flakes, or mica flakes optionally coated with a uniform metallic oxide layer, with a uniform layer of a low-solubility iron compound convertible into Berlin blue [ferric hexacyanoferrate(II)], and then converting this layer into Berlin blue.

9 Claims, No Drawings

COLORED PIGMENTS

BACKGROUND OF THE INVENTION

This invention relates to novel blue mica flake pigments.

Colored pigments and more particularly colored lustrous pigments are of increasing interest in a great variety of fields, for example, in cosmetics and as additives to synthetic resins, varnishes and paints.

A number of mica flake lustrous pigments and naceous pigments are known. The colors of these pigments are normally produced by interference, but they can also be based partially on colored metallic oxide additives. The thus-attainable play of colors is, however, limited. Pigments having blue or blue-tinged color tones in a satisfactory nuancing have not been attainable heretofore.

Processes are known (see German Patent No. 1,192,353 and the corresponding U.S. Pat. No. 2,995,459), according to which lustrous pigments can be directly dyed by the precipitation thereon of colored precipitates. However, these conventional processes are unsuitable for a precipitation of Berlin blue, because the latter forms colloidal deposits during direct precipitation, which settle only partially or not at all on the flakes of the pigment to be dyed. This leads to irreproducible batches, to considerable difficulties during filtering, and, in particular, no nacreous luster effect can be obtained in this way. However, by adhering to the conditions of the process of this invention, colored pigments are obtained having a high gloss and a strong chroma.

In accordance with this invention, mica flake pigments with blue color tones are obtained. These pigments have a very high color strength [chroma], and can be produced in a palette of staggered color nuances of blue tones or blue-tinged colors. Such color tones have heretofore been unaccessible. Such pigments are of special interest in the cosmetic field, because the dye employed in this invention is permitted for this application.

SUMMARY OF THE INVENTION

Accordingly, in its composition aspect, this invention relates to novel mica flake pigments having ferric hexacyanoferrate(II) [Berlin blue] as a color-imparting coating thereon.

In its process aspect, this invention relates to a process for the production of such novel colored pigments wherein mica flakes or mica flakes coated with a uniform metallic oxide layer are coated with a uniform layer of a low-solubility iron compound which is convertible into Berlin blue and thereafter converting the iron compound into a microscopically smooth and uniform coat of Berlin blue, which firmly adheres to the substrate.

DETAILED DISCUSSION

The novel pigments of this invention can be manufactured from all mica flake pigments. Thus, in addition to uncoated mica flakes, it is possible to utilize as the starting material mica flakes coated with a uniform layer of a metallic oxide. Such pigments are commercially available and described, for example, in German Patent No. 2,009,566. Normally, mica flakes are employed having a diameter of about 5 – 200 microns and a thickness of between 0.1 and 5 microns, preferably about 0.5 micron.

Mica flakes coated with titanium dioxide and/or titanium dioxide hydrate and/or zirconium dioxide or zirconium dioxide hydrate are utilized primarily as metallic oxide coated mica flakes because of the advantageous index of refraction of these compounds. A mica flake pigment used particularly advantageously is, for example, mica flakes having a diameter of about 5–50 microns and a thickness of about 0.5 micron uniformly coated with an optionally hydrated titanium dioxide layer, the mica surface containing about 50–300 mg. of $TiO_2$ per square meter. These conventional nacreous pigments exhibit varying colors, depending on the layer thickness of the precipitated $TiO_2$ and/or $ZrO_2$ layer. Normally, calcined products are involved. However, it is of course also basically possible to utilize all other coated mica flake pigments, especially also those having different layer thicknesses of $TiO_2$ and/or $ZrO_2$. These starting materials include all nacreous pigments containing in the coats provided on the mica flakes further additives of coloring metallic oxides, e.g., of iron, nickel, cobalt, chromium or vanadium. Optionally, these layers can also contain additionally non-coloring metallic oxides, e.g., aluminum oxide or antimony oxide. These pigments are known and described, for example, in German Pat. Nos. 1,467,468 and 1,959,998. See also U.S. Pat. Nos. 3,553,001 and 3,711,308 and references cited therein for examples of suitable starting materials.

According to this invention, a coating of Berlin blue is applied to these starting pigments. As is known, Berlin blue is formed most simply by combining a hexacyanoferrate with an iron salt. It is particularly advantageous for the production of the pigments according to this invention to form the Berlin blue coat so that first the pigment flakes are coated with a layer of a sparingly soluble iron compound convertible to Berlin blue, for example by oxidation and/or by reaction with a hexacyanoferrate. In this connection, it is essential that a low-solubility iron compound be utilized which can be precipitated in a smooth layer on the pigment particles. It was found that generally iron(II) salts form smooth layers more readily than iron(III) salts. Trivalent iron compounds easily lead to colloidal deposits, so that the conductance of the reaction becomes more difficult.

Suitably, the procedure employed is such that the layer consisting of the low-solubility iron compound convertible into Berlin blue is precipitated onto the mica flakes, optionally metallic oxide coated, which are present in an aqueous suspension. During this step, at least one of the precipitating reactants is added so gradually that essentially all of the entire thus-formed deposit is directly precipitated onto the flakes. It is especially advantageous to employ a sparingly soluble iron compound which is convertible into Berlin blue by oxidation and/or reaction with a water-soluble hexacyanoferrate. If the deposited layer of sparingly soluble iron compound is iron(II) hexacyanoferrate(II), only an oxidation is required. In all other cases, a water-soluble hexacyanoferrate, preferably potassium hexacyanoferrate(II), is allowed to contact the thus-obtained, coated particles, in an aqueous suspension, optionally while treating the reaction mixture simultaneously and/or subsequently with an oxidizing agent. The fixation of the Berlin blue layer by means of a previously applied layer of iron(II) phosphate or iron-(III) oxide hydroxide is particularly advantageous.

Thus, several processes can be employed to obtain Berlin blue coated pigments in accordance with this invention. These processes differ essentially with respect to the valences of the iron salts utilized. The effect attainable is the same in all cases, but the colored coatings vary in dependence on the methods used with respect to color tone and chroma, so that here a further possibility presents itself for broadening the range of the color palette.

Thus, according to the process of this invention, the novel pigments can be produced by any of the following:

a. coating the starting mica flakes with a sparingly soluble iron(II) salt, reacting the precipitated iron(II) salt formed on the mica with hexacyanoferrate(II) to form a colorless coating of iron(II) hexacyanoferrate(II), and then oxidizing the hexacyanoferrate(II) coating to Berlin blue; or b. forming a layer of white iron(II) hexacyanoferrate(II) on the starting mica flakes by direct precipitation onto the starting mica flakes, followed by oxidation to Berlin blue as in (a); or c. coating the starting mica flakes with a sparingly soluble iron(II) salt as in (a), oxidizing the iron(II) salt to the iron(III) salt, and reacting the iron(III) salt with a hexacyanoferrate(II) to form Berlin blue; or d. coating the starting mica flakes with a sparingly soluble iron(III) salt and reacting the precipitated iron(III) salt with hexacyanoferrate(II) to form Berlin blue; or e. coating the starting mica flakes with a sparingly soluble iron(II) salt and reacting the precipitate with a hexacyanoferrate(III) to form Berlin blue.

Methods (a) through (c) are preferred in practice and for technical-scale operations. In method (d), it is difficult to coat the starting pigment, since precipitates of trivalent iron compounds have the tendency to assume the colloidal form. In method (e), difficulties are encountered in maintaining the precipitated iron(II) salt in this oxidation stage, since it is subjected to agitation during the further reaction and thus normally exposed to air. Therefore, it is technically expensive to prevent the oxidation. Moreover, the oxidized proportion of the precipitated iron(II) salt is unavailable for the formation of Berlin blue, since in such case a soluble compound is formed, as is known. Moreover, the hexacyanoferrate(II) used in method (e) is relatively poisonous, since, in contrast to hexacyanoferrate(II), it is easily decomposed with the formation of hydrocyanic acid.

As layers of iron compounds sparingly soluble in water preferably iron(II) phosphate, iron(III) phosphate, iron(II) hydroxide, iron(III) hydroxide, iron(III) oxide hydroxide, iron(II) carbonate, or basic iron(III) acetate or mixtures thereof are precipitated. Iron compounds of low solubility are those whose water solubility is measurable, e.g., at least $10^{-6}$ g./l., but less than 0.5 g./l., preferably less than 0.1 g./l., at 20°C. They include the salts and oxides and/or hydroxides and/or oxide hydroxides.

The precipitation of these sparingly soluble iron compounds is most advantageously effected under conditions whereby a uniform and coherent layer thereof is formed on the mica flakes. This is optimally possible, for example, by starting with a solution of an iron(II) salt, especially iron(II) sulfate. Ammonium iron(II) sulfates or iron(II) halides are also suitable. Basically, however, it is also possible to utilize iron(III) salts, such as, for example, $FeCl_3$. Advantageously, aqueous, optionally acidified solutions of these iron salts are added to an aqueous slurry of the mica flakes simultaneously with an aqueous solution providing the anion of the sparingly soluble compound to be formed. The concentration of the iron salt solutions ranges normally between about 5 and 500 g./l., preferably about 10 – 300 g./l. The precipitation takes place from an aqueous solution at pH values of above 3, preferably between 5 and 9. If, during this reaction, iron(II) hexacyanoferrate(II) is precipitated, so that subsequently only an oxidation is required, the precipitation can also occur at lower pH values, e.g., 1 to 6.5. The necessary pH values are preferably set by adding alkali hydroxide or ammonium hydroxide or also by gaseous ammonia. The pH is maintained as constant as possible during the precipitation. Donors of the anions for the formation of the sparingly soluble iron compound are preferably alkali hydroxides or alkali salts, e.g., phosphates, carbonates, acetates or hexacyanoferrates. Normally, sodium salts and potassium salts are preferred. If the anion required to form the layer-forming sparingly soluble compound is supplied by the addition of an acid (e.g., phosphoric acid or $CO_2$), it is necessary to absorb the thus-liberated acid, in order to avoid a shift in the pH. This can be done, for example, by neutralizing with alkali or ammonia, or by adding a buffer. It is advantageous in most cases to conduct the precipitation of the sparingly soluble compound in the presence of a buffer salt. Such buffer systems are, for example, phosphate, acetate and/or glycocoll buffers of conventional composition. These buffers can either be provided advantageously in the pigment suspension or can be introduced with the precipitation solution.

The precipitation conditions are adjusted conventionally so that the thus-formed precipitate is immediately and quantitatively deposited on the mica flakes. In this connection, it is important that an excess of metallic ions be avoided in the suspension. Therefore, per unit time, only such an amount is to be added for reaction purposes which can be absorbed per unit time as the sparingly soluble iron compound onto the surface of the mica flakes to be coated. Only by preventing particles from being precipitated into the suspension rather than being bound to the pigment surface is it possible to obtain homogeneous and amorphous layers having a uniform and identical layer thickness, which are necessary in order for the pigments to have a high lustrous effect and a good nacreous property. More detailed information regarding the process for precipitating such layers can be found, for example, in German Patent No. 2,009,566, as well as in German Patent Application No. P 22 44 298 and U.S. application Ser. No. 390,252, filed Aug. 21, 1973, whose disclosures are incorporated herein by reference. The layer thickness of this initially precipitated uniform coating of a sparingly soluble iron compound is not critical, but ranges generally between 0.1 and 150 nm.

The thus-precipitated layer, which consists preferably at least partially of an iron(II) compound or of FeOOH, can react, unless it is iron(II) hexacyanferrate(II), with a soluble hexacyanoferrate to form Berlin blue. This reaction takes place normally at a pH of between 3.0 and 6.5. As stated above, a reaction with a hexacyanoferrate containing bivalent iron is preferred, for these salts are more stable and less poisonous than the corresponding iron(III) compoonds. Moreover, hexacyanoferrates containing trivalent iron form a soluble compound with iron(III) ions present in the layer, which compound is washed out and thus is lost to the pigment. Preferred as hexacyanoferrates(II) are water-soluble alkali and alkaline earth hexacyanoferrates, e.g., $Na_4[Fe(CN)_6]$, $K_4[Fe(CN)_6]$, $(NH_4)_4[Fe(CN)_6]$, as well as the corresponding calcium and strontium salts. Basically, however, the corresponding hexacyanoferrates(III) can also be used in case iron(II) compounds were precipitated on the mica flakes before.

The aqueous solution of the hexacyanoferrate is advantageously added gradually and/or in incremental portions. The reaction speed slowly decreases during the course of the reaction, since the sparingly soluble iron hexacyanoferrate formed on the surface impedes the further progress of the reaction.

if the layer of the sparingly soluble iron compound on the pigment particles and the hexacyanoferrate added thereto both initially contain only bivalent iron, iron-(II) hexacyanoferrate(II) is formed as a white precipitate on the particles to be coated in the shape of a crystalline, smooth coating. However, this coating can be oxidized extremely readily and in such case passes over into the desired Berlin blue [iron(III) hexacyanoferrate(II)]. The same, of course, also holds true for the precipitate of iron(II) hexacyanoferrate(II) obtained by direct precipitation, e.g., from iron(II) sulfate and potassium hexacyanoferrate(II). This oxidation is most simply achieved already by agitating the solution in the presence of atmospheric oxygen, or, for example, also during drying of the isolated, coated pigment in the air. It is also possible to employ a chemical oxidizing agent, for example, hydrogen peroxide, alakli nitrate or ammonium nitrate, potassium chlorate, sodium chlorate, chlorine and/or nitric acid. The oxidizing agents can be introduced in a stoichiometric amount as well as in an excess. The reaction conditions are known from the literature and do not deviate from standard methods.

The reaction with the hexacyanoferrates takes place suitably directly in the reaction mixture produced when coating the starting material with the sparingly soluble iron compound. A previous isolation of the coated particles is normally unnecessary.

It is advantageous to add, before coating the starting material, a preferably nonionic wetting agent to the aqueous slurry of mica flakes. Suitable, are, for example, polyalkylene glycol, polyoxyethylene fatty alcohol ether, polyoxyethylene fatty acid ester, alkylphenol polyglycol ether and hydroxyallkyl cellulose, e.g., hydroxypropylcellulose, wetting agents.

The wetting agent is normally added in an amount of between 0.01 and 10%, based on the suspension of mica flakes employed. The pigments obtained when these wetting agents are used are distinguished by a particularly high luster and again increased color strength [chroma].

The layer thickness of the Berlin blue on the pigments is dependent on the layer thickness of the previously precipitated low-solubility iron compound. In general, layer thicknesses of from 0.1 to 150 nm., preferably from 1 to 70 nm., can be produced. The pigments of the present invention normally contain 0.1–25%, preferably about 1–15%, of Berlin blue, based on the total pigment weight.

According to the process of this invention, pigments are obtained having a microscopically smooth and uniform coat of Berlin blue which firmly adheres to the substrate. The smoothness and uniformity of the coat is to be shown by microscopic inspection, whereby no blanks and no differences in thickness of the coat are to be seen. The coated particles can be readily filtered and can be washed without difficulty. The thus-washed pigments are subsequently dried, advantageously at a temperature below 250° C. under atmospheric pressure, or at a correspondingly lower temperature under reduced pressure.

If uncolored nacreous pigments are used as the starting material, nacreous pigments are obtained according to this invention which have a radiantly blue color and a high brilliance. If the starting material consists of nacreous pigments which, in turn, already exhibit interference colors, various shades of blue are obtained, depending on the basic pigment employed. Thus, for example, a nacreous pigment having a blue interference color shows, when coated with Berlin blue, an essentially deeper, more vigorous blue tone than a nacreous pigment with a silver luster, coated with Berlin blue according to this invention, while a correspondingly treated macreous pigment having a red interference color has a more reddish tone of blue and a nacreous pigment with a green interference color shows a more greenish tone of blue. However, in the angle of reflection, the interference color of the starting material employed becomes apparent. Thereby, scintillating effects with two-color iridescence are obtained with highly striking appearance.

If the starting material consists of nacreous pigments dyed by means of additives, e.g., metallic oxides, here again a great variety of blue tones is produced or a corresponding shifting of the basic powder color is achieved by the Berlin blue. When coating nacreous pigments having a yellow powder color with Berlin blue, the results are, for example, depending on the amount of Berlin blue, nacreous pigments having olive-green tones in various nuances.

In contrast thereto, if the starting material is uncoated mica without nacreous luster, blue pigments are obtained which are of interest, due to their transparent character, for special fields of application, for example in the varnish industry.

All pigments can be used just as those known heretofore, wherein utilization in the cosmetic field is particularly attractive. In this case, the nacreous pigments are added normally in amounts of between 0.1 and 80% by weight. Suitable forms of application are, for example, powders, ointments and lubricating sticks, e.g., eyeshadow sticks (pigment content about 5–15%), pressed-powder eyeshadow (pigment content about 20–70%), liquid preparations for eyeshadow and eyeliner (pigment content about 7–15%), lipsticks (pigment content about 10–20%), lip gloss creams to brush on (pigment content about 10–15%), makeup in stick form (pigment content about 15–25%), makeup powder compacts (pigment content about 10–50%), makeup emulsions (pigment content about 5–10%), makeup moisturizing gel (pigment content about 1–5%), bubble bath concentrates with color luster (pigment content about 0.1–2%).

An advantage of the pigments of this invention when used in the cosmetic field resides in the excellent colorful luster produced, which is desirable for many decorative cosmetics. Furthermore, the pigments of this invention are distinguished in that they can be readily used as masterbatches because the coloring and luster-imparting components, which would ordinarily require the use of separate coloring and lustrous pigments, are combined in one substance. Since the coloring agents are naturally very finely distributed, due to the manner in which they were produced, the usual detour route of a mechanical premixing step is eliminated. Furthermore, it is easily possible to attain iridescent color effects in the products in which the pigments of this invention are incorporated. Finally, the simple and advantageous combination of the novel pigments with conventional synthetic nacreous pigments, e.g., mica/titanium dioxide, bismuth oxychloride and guanine, is important. Simply by mixing and blending the powdery novel pigments with the conventional nacreous powders, it is possible to vary the color and luster in any manner desired, adapted to fashion requirements.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The temperatures hereinbelow are set forth in degrees Celsius.

EXAMPLE 1 a. 15 kg. of mica of the muscovite type, particle size about 10–40 $\mu$, specific surface area about 3.5 m²/g. is suspended in such a quantity of desalted water in a 400 liter vessel that a 10% suspension is produced. The suspension is brought to pH 2.2 by adding a 25% hydrochloric solution of titanium tetrachloride (250 g. TiCl$_4$/l. and 30 g. HCl/l.) and then stirred and heated to a temperature of 75°. The solution is maintained at this temperature during the entire coating process.

The 25% acidic titanium tetrachloride solution is fed to the suspension at a rate of 15 l./h. The pH is kept constant by adding a 35% aqueous NaOH solution. The coating step is terminated upon the consumption of 1 kg. of titanium tetrachloride per kg. of mica.

The thus-obtained pigment is washed with desalted water, dried, and annealed for 30 minutes at 950°. The pigment appears silver in incident light.

b. A suspension is prepared from 30 g. of the thus-produced silvery pigment and 300 ml. of water and heated to 70°. 2.1 g. of Na$_2$HPO$_4$ . 12 H$_2$O and 0.8 g. of CH$_3$COONa . 3 H$_2$O are dissolved in the suspension. Under constant agitation, a solution of 3.05 g. of (NH$_4$)$_2$Fe(SO$_4$)$_2$ . 6 H$_2$O in 100 ml. of water is then added to the reaction mixture. The feeding rate is 130 ml./h.

During the reaction, a pH of 4.0–4.5 is maintained. The color of the pigment remains unchanged, in spite of the formation of an Fe(II) phosphate layer. After about 15 minutes, a solution of 2.43 g. of K$_4$[Fe(CN)$_6$] . 3 H$_2$O in 100 ml. of water is gradually introduced. The pH of the suspension rises during this step to 5.5–6.0, and the pigment assumes a slightly greenish color. After another 15 minutes, the suspension is brought to pH 3 by adding 2.5% strength hydrochloric acid. Then, 0.12 g. of KClO$_3$, dissolved in 5 ml. of water, is added as the oxidizing agent. The suspension is stirred for about 1 hour and thereafter allowed to stand overnight. On the following day, the product is filtered off and washed with water, whereupon it is dried in a drying chamber at 120°. The blue pigment contains about 5.6% by weight of Berlin blue, 26.4% of TiO$_2$, and 68% of mica.

EXAMPLE 2

30 g. of the mica/TiO$_2$ pigment obtained according to Example 1(a) is coated with Fe(II) phosphate analogously to Example 1(b). Subsequently, a solution of 2.43 g. of K$_4$[Fe(CN)$_6$] . 3 H$_2$O in 100 ml. of water is added dropwise under constant agitation. By the simultaneous dropwise addition of 1% hydrochloric acid, the pH is maintained constant at 4.0. Already during the reaction the pigment color changes toward a strong blue which, at the end of the reaction, is further deepened by adding HCl and KClO$_3$ analogously to Example 1(b). The product is worked up in correspondence with Example 1(b); it contains about 5.6% by weight of Fe$_4$[Fe(CN)$_6$]$_3$, about 68% by weight of mica, and about 26.4% by weight of TiO$_2$.

EXAMPLE 3

30 g. of muscovite having a diameter of 10–40 $\mu$ and a thickness of about 0.5 $\mu$ is suspended in 200 ml. of fully desalted water while adding 30 mg. of a nonionic wetting agent on the basis of alkylphenol polyglycol ethers. The suspension is heated to 70° and mixed with 9 g. of Na$_2$HPO$_4$ . 12 H$_2$O and 3 g. of CH$_3$COONa . 3 H$_2$O. Under vigorous agitation, a solution of 6.6 g. of FeSO$_4$ . 7 H$_2$O and 0.15 ml. of H$_2$SO$_4$ in 150 ml. of water is added in metered amounts to this suspension within 45 minutes. During the precipitation, the pH drops to about 4. Thereafter, a pH of 3.8 is set by adding dilute hydrochloric acid (3%). Within one hour, a solution of 7.5 g. of K$_4$[Fe(CN)$_6$] . 3 H$_2$O in 150 ml. of water is fed gradually in metered quantities. At the end of the reaction, the oxidizing step is conducted by adding 0.33 g. of KClO$_3$ at a pH of 3.0. The suspension is agitated for one hour and finally allowed to stand overnight. The pigment is filtered off, washed thoroughly with fully desalted water, and dried in a drying chamber at 130°. The pigment contains about 15% by weight of Berlin blue (corresponding to a layer thickness of about 30 nm.) and about 85% by weight of mica.

EXAMPLE 4

The starting material employed is an olive-green mica flake pigment produced according to German Patent No. 1,959,998, carrying two coats on the mica, the lower coat having a thickness of about 50 nm. and consisting of about 95% by weight TiO$_2$ and about 5% by weight Cr$_2$O$_3$, and the upper coat having a thickness of about 100 nm. and consisting solely of TiO$_2$.

25 kg. of this pigment is suspended in 280 l. of desalted water and heated to 85° after adding 23 g. of a nonionic wetting agent on the basis of alkylphenol polyglycol ethers. After this temperature has been reached, 2.5 kg. of Na$_2$HPO$_4$ . 12 H$_2$O and 835 g. of CH$_3$COONa . 3 H$_2$O are added thereto. Then, a solution of 1.84 kg. of FeSO$_4$ . 7 H$_2$O and 40 ml. of sulfuric acid in 40 l. of water is gradually introduced. The mixture is agitated for 30 minutes; then, a pH of 3.7 is set and a solution of 2.08 kg. of K$_4$[Fe(CN)$_6$]. 3 H$_2$O in 30 l. of water is gradually added thereto in incremental portions. By the simultaneous addition of 2.5% strength hydrochloric acid, the pH of the suspension is lowered during the reaction to such an extent that a pH of 3.2 is reached at the end of the reaction. The reaction time is about 2 hours. The oxidation to Berlin blue is accomplished by stirring air into the reaction mixture for about 2 hours at a temperature of 85°. The pigment is worked up as described above. The pigment has a lively green luster, with a greenish blue color of the powder, and contains 5.5% by weight of Berlin blue, 0.9% $Cr_2O_3$, 52.1% $TiO_2$, and 41.5% mica.

EXAMPLE 5

54 kg. of the pigment obtained according to Example 1(a) is suspended in 600 l. of water while adding 50 g. of a nonionic wetting agent on the basis of alkylphenol polyglycol ethers, and the suspension is heated to 70°. Then, 5.4 kg. of $Na_2HPO_4 . 12 H_2O$ and 1.8 kg. of $CH_3COONa . 3 H_2O$ are added thereto. Thereafter, a solution of 3.96 kg. of $FeSO_4 . 7 H_2O$ and 90 ml. of sulfuric acid in 90 l. of water is gradually added in metered quantities. During the precipitation of the iron phosphate, the pH of the suspension drops to about 4.5. The mixture is agitated for one-half hour, then the pH is set to 3.7 by adding 2.5% strength HCl, and a solution of 4.5 kg. of $K_4[Fe(CN)_6] . 3 H_2O$ in 60 l. of water is gradually added in incremental portions. By the simultaneous addition of 2.5% strength HCl, the pH is gradually lowered during the reaction so that a pH of 3.2 is attained at the end of the reaction. The reaction time is about 2 hours. During the reaction of the precipitated iron phosphate with hexacyanoferrate, air is stirred into the mixture as the oxidizing agent, so that the desired deep blue color dye is formed immediately. The suspension is agitated for about 1 hour and then allowed to stand. The pigment is filtered off, washed thoroughly with water, and dried at 130° in a drying chamber. This pigment contains 5.5% of Berlin blue, 68% of mica, and 26.5% of $TiO_2$.

EXAMPLE 6

The starting material is a golden yellow mica/$TiO_2$ pigment containing $Fe_2O_3$ in the $TiO_2$ layer to deepen the color. This pigment contains about 58% by weight of mica, 40% by weight of $TiO_2$, and 2% by weight of $Fe_2O_3$.

54 kg. of this golden yellow nacreous pigment is suspended in 600 l. of water analogously to Example 5 and coated with Berlin blue, thus obtaining a pigment having a bluish-olive green powder color exhibiting a lively golden glitter in the angle of reflection. The pigment contains about 5.5% by weight of Berlin blue, 54.7% by weight of mica, 37.9% by weight of $TiO_2$, and 1.9% by weight of $Fe_2O_3$. With the use of the same method, a mica pigment can be coated with Berlin blue which contains, in addition to $Fe_2O_3$, $ZrO_2$ in place of $TiO_2$, thus producing a pigment having a bluish-olive green powder color showing a yellow glitter in the angle of reflection. This pigment likewise contains about 5.5% by weight of Berlin blue.

EXAMPLE 7

The starting material is a mica/$TiO_2$ pigment showing a violet interference color with a $TiO_2$ content of 41% (layer thickness of $TiO_2$ about 100 nm.).

54 kg. of this pigment is suspended in 600 l. of water analogously to Example 5 and coated with Berlin blue, thus obtaining a deep blue pigment with violet iridescence in the angle of reflection. This pigment contains about 5.5% by weight of Berlin blue.

EXAMPLE 8

6 kg. of muscovite having a platelet diameter of about 10–30 $\mu$ and a thickness of about 0.5 $\mu$ is suspended in 200 l. of water. The suspension is heated to 70° and the pH set to 6.0 with sodium hydroxide solution or hydrochloric acid. While introducing a vigorous stream of air into the mixture, a solution of 440 g. of $FeSO_4 . 7 H_2O$ and 4.4 ml. of $H_2SO_4$ in 8 l. of water is gradually added, during which time the pH of the suspension is maintained at a constant value by the simultaneous feeding of dilute sodium hydroxide solution. The thus-formed $\alpha$-FeOOH is deposited on the mica flakes as a smooth, uniform layer.

The thus-coated mica flakes are reacted analogously to Example 5 with potassium hexacyanoferrate, thus forming Berlin blue directly. After washing and drying, a pigment is obtained having a deep blue color, containing about 5.5% by weight of Berlin blue and 94.5% by weight of mica.

Analogously, the pigment can also be produced by precipitating, in place of $\alpha$-FeOOH, a layer of $\gamma$-FeOOH at room temperature and a pH of 7.5.

EXAMPLE 9

Analogously to Example 8, a nacreous pigment on the basis of $TiO_2$-coated mica flakes, consisting of 50% $TiO_2$ and 50% mica, and showing a blue interference color, is coated with Berlin blue. The thus-produced nacreous pigment possesses, with a deep blue color of the powder, a vigorous, blue luster and contains, in addition to 5.6% by weight of Berlin blue, 47.2% by weight of mica and 47.2% by weight of $TiO_2$.

EXAMPLE 10

30 g. of the mica/$TiO_2$ pigment obtained according to Example 1(a) is suspended in 300 ml. of fully desalted water, and the suspension is heated to 70°. Then, by adding an acidic $TiCl_4$ solution analogously to Example 1(a), a pH of about 5 is set. Under agitation, a solution of 2.2 g. of $FeSO_4 . 7 H_2O$ and 0.1 ml. of concentrated sulfuric acid in 150 ml. of water and a solution of 2.43 g. of $K_4[Fe(CN)_6] . 3 H_2O$ in 150 ml. of water are added simultaneously to this suspension by gradual feeding at the same flow rate. By the addition of 3% sodium hydroxide solution at the same time, the pH is kept constant at 5. The pigment particles assume a witish green color during the coating step. 0.12 g. of $KClO_3$ is added thereto, and a pH of 3 is set by the addition of 10% hydrochloric acid. The suspension is maintained for several hours at 70° and constantly agitated. The thus-formed Berlin blue imparts a vigorous blue color to the pigment particles, the silvery nacreous luster being retained. The pigment is filtered, washed, and dried analogously to Example 1(b). It contains about 5.6% by weight of Berlin blue, 26.4% of $TiO_2$, and 68% of mica.

USE OF THE PIGMENTS

A. Eyeshadow Stick with Colorful Nacreous Luster

| | |
|---|---|
| Pigment according to Example 1 | 10 % |
| Castor oil | 15 % |
| Perfume | 0.5 % |
| Wax/oil base composition | 74.5 % |
| Components of the wax/oil base composition: | |
| Beeswax | 12.5 % |
| Carnauba wax | 6.2 % |
| Hard paraffin | 6.2 % |
| Cetyl alcohol | 3.7 % |

-continued

| | |
|---|---|
| Vaseline, white | 2.5 % |
| Lanolin | 2.5 % |
| Paraffin | 1.2 % |
| Isopropyl myristate | 10.0 % |
| Castor oil | 55.05 % |
| Propyl p-hydroxybenzoate | 0.1 % |
| Antioxidant | 0.05 % |

B. Pressed-Powder Eyeshadow with Colorful Nacreous Luster

| | |
|---|---|
| Pigment according to Example 4 | 50 % |
| Talc | 29.5 % |
| Kaolin | 3 % |
| Calcium stearate | 5 % |
| Corn starch | 3 % |
| Isopropyl lanolate | 6 % |
| Isopropyl myristate | 3 % |
| Perfume | 0.5 % |

C. Eyeshadow and Eyeliner, Liquid

| | |
|---|---|
| Pigment according to Example 6 | 12 % |
| 1,2-Propylene glycol | 20 % |
| Magnesium aluminum silicate | 2.5 % |
| Water | 65.5 % |

D. Nacreous Bubble Bath Concentrate

| | |
|---|---|
| Pigment according to Example 8 | 0.2 % |
| Silicic acid, finely dispersed, suspended 1+9 with water | 10 % |
| Water, fully desalted | 8.3 % |
| Citric acid | 1 % |
| Perfume, water-soluble | 1.5 % |
| Sodium lauryl ether sulfate | 15 % |
| Ammonium fatty alcohol ether sulfate | 60 % |
| Coconut fatty acid diethanolamide | 4 % |

E. Button Panel

The pigment of Example 9 is suspended in twice the amount of a mixture of equal parts of n-butyl acetate, ethylene glycol monoethyl ether, and dibutyl phthalate. 2.5 g. of the thus-produced suspension is combined with 250 g. of an unsaturated polyester resin, and the charge is cured, after adding 0.4% of a 1% solution of cobalt octoate and 2.4% of a 50% strength ketone peroxide, in a centrifugal drum. After curing, a polyester panel is obtained having a uniform nacreous character with a greenish blue luster from which buttons can be produced, for example.

F. Pigmenting of Thermoplastics 10 kg. of polystyrene is combined with 50 g. of dibutyl phthalate and intensively mixed for 15 minutes. After adding 100 g. of the pigment obtained according to Example 5, the mixture is thoroughly shaken for another half hour. The thus-obtained blend is then molded, in a screw-type injection molding machine, at about 200° C. to stepped platelets having a very high nacreous luster and an attractive blue color.

G. Pigmented Varnishes 30 parts of collodion cotton (22% in butyl acetate)
40 parts of oil-extended alkyd resin on the basis of synthetic fatty acids (75% in mineral spirits)
10 parts of toluene
4 parts of glycolic acid butyl ester
2 parts of cobalt drier are combined and agitated. Two parts of the pigment produced according to Example 8 is moistened with 4 parts of butyl acetate and introduced into the charge. After thorough mixing, the varnish is sprayed on primed metal sheets. During drying, a smooth film is obtained having a very high nacreous luster.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A colored mica flake pigment having a layer of ferric hexacyanoferrate(II) on the mica flakes as a color-imparting uniform coating.

2. A blue pigment according to claim 1 containing, as its sole colored layer, up to 25% by weight of ferric hexacyanoferrate(II) as a coating of a uniform thickness of about 0.1 to 150 nm.

3. A pigment according to claim 1 wherein the mica flakes have a uniform coating of $TiO_2$ or $ZrO_2$ or a hydrate thereof beneath the ferric hexacyanoferrate.

4. A pigment according to claim 3 wherein the coating beneath the ferric hexacyanoferrate(II) is titanium dioxide.

5. A pigment according to claim 1 wherein the ferric hexacyanoferrate(II) is the sole coating on the mica flakes.

6. A pigment according to claim 1 wherein the mica flakes have a diameter of 5–50 microns and a thickness of about 0.5 microns and are uniformly coated with a layer of 50–300 mg. of titanium dioxide per square meter of surface beneath the layer of ferric hexacyanoferrate(II).

7. A pigment according to claim 2 containing 1–15% by weight of ferric hexacyanoferrate(II) as a layer of a thickness of from 1 to 70 nm.

8. A cosmetic preparation containing therein a pigment according to claim 1.

9. A cosmetic preparation according to claim 8 wherein the preparation is eyeshadow in stick, pressed powder or liquid form, containing about 5–15%, 20–70% and 7–15% by weight, respectively, of the pigment.

* * * * *